United States Patent [19]

Holan et al.

[11] 4,277,490
[45] Jul. 7, 1981

[54] INSECTICIDAL 1-(2-NAPHTHYL)-CYCLOBUTANE CARBOXYLATE

[75] Inventors: George Holan, Brighton; Reimund A. Walser, Box Hill, both of Australia

[73] Assignee: Commonwealth Scientific and Industrial Research Organization, Australia

[21] Appl. No.: 98,715

[22] Filed: Nov. 30, 1979

[30] Foreign Application Priority Data

Dec. 4, 1978 [AU] Australia .............................. PD6995

[51] Int. Cl.³ ...................... A01N 43/30; C07C 69/74; C07C 121/75; C07D 305/10
[52] U.S. Cl. ............................ 424/282; 260/340.5 R; 260/347.4; 260/465 D; 424/285; 424/304; 424/308; 560/100; 562/490
[58] Field of Search .................... 260/465 D, 340.5 R, 260/347.4; 560/100; 424/304, 308, 282, 285

[56] References Cited

U.S. PATENT DOCUMENTS 4,053,631 10/1977 Schrider .............................. 424/304
4,130,656 12/1978 Greuter et al. ...................... 424/304

FOREIGN PATENT DOCUMENTS 1521939 8/1978 United Kingdom .

OTHER PUBLICATIONS

Holan et al., *Nature*, vol. 272, pp. 734–736 (1978).

*Primary Examiner*—Dolph H. Torrence
*Attorney, Agent, or Firm*—Bacon & Thomas

[57] ABSTRACT

New compounds are described that fall within the general formula I

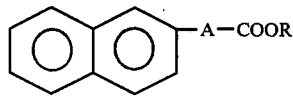

wherein R is hydrogen, or a lower alkyl group, or one of the following groups:
(a) 3-phenoxybenzyl
(b) 2-benzyl-4-furylmethyl
(c) α-cyano-3-phenoxybenzyl
(d) 3,4-methylenedioxybenzyl
(e) α-ethynyl-3-phenoxybenzyl
(f) α-cyano-3-(4-chlorophenoxy)-benzyl and A is one of the groups X or Y

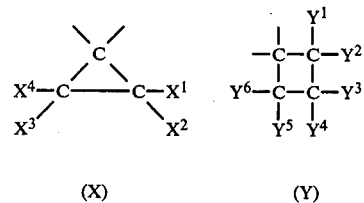

(X)           (Y)

wherein $X^1$, $X^2$, $X^3$ and $X^4$ are the same or different groups and each is hydrogen or fluoro, chloro, bromo or methyl group, with the proviso that if $X^1$ or $X^3$ is a fluoro group then $X^2$ or $X^4$ should not be a bromo group; and wherein $Y^1$, $Y^2$, $Y^3$, $Y^4$, $Y^5$ and $Y^6$ are the same or different groups and each is hydrogen or a fluoro, bromo, chloro or methyl group.

Processes of making the compounds are described. The compounds in which $R^3$ is one of groups (a) to (f) are insecticides and insecticidal methods and compositions containing them are described.

21 Claims, No Drawings

INSECTICIDAL 1-(2-NAPHTHYL)-CYCLOBUTANE CARBOXYLATE

This invention relates to new insecticidal compounds, methods of preparing these compounds and to new insecticidal compositions containing the compounds.

Throughout this specification, where the context permits, the word "insect" is used in its broad common usage and includes spiders, mites, nematodes and other pests which are not classed as insects in the strict biological sense. Thus the term implies reference not only to those small invertebrate animals belonging mostly to the class Insecta, comprising six-legged, usually winged forms, such as beetles, bugs, flies and the like, but also to other allied classes of arthropods whose members are wingless and usually have more than six legs, such as spiders, wood lice and the like, and especially to the order Acaridae which includes the mites and ticks. The words "insecticide" and "insecticidal" are similarly used.

The compounds provided by this invention have the general formula I

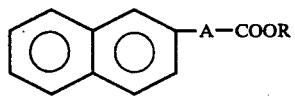

wherein R is hydrogen, or a lower alkyl group, or one of the following groups (a) to (f):

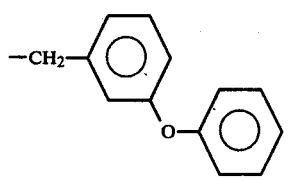 (a)

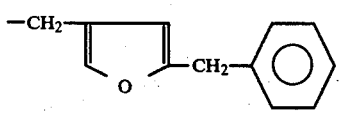 (b)

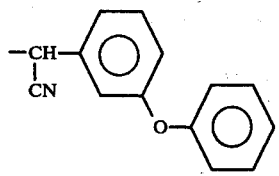 (c)

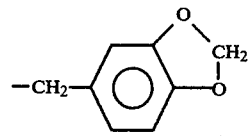 (d)

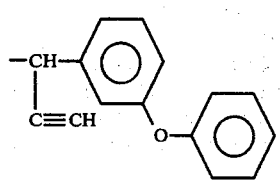 (e)

-continued

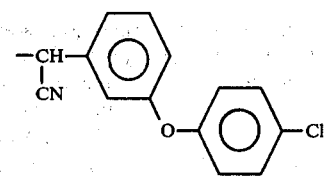 (f)

and A is one of the groups X or Y

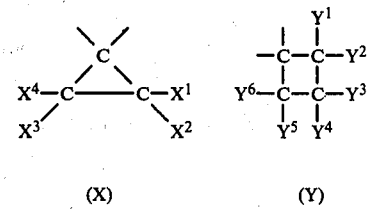

wherein $X^1$, $X^2$, $X^3$ and $X^4$ are the same or different groups and each is hydrogen or fluoro, chloro, bromo or methyl group, with the proviso that if $X^1$ or $X^3$ is a fluoro group then $X^2$ or $X^4$ should not be a bromo group; and wherein $Y^1$, $Y^2$, $Y^3$, $Y^4$, $Y^5$ and $Y^6$ are the same or different groups and each is hydrogen or a fluoro, bromo, chloro or methyl group.

Known compounds which can be regarded as related to the compounds of formula I are those in which the groups (a) to (e) are present as esterifying groups with chrysanthemic acid in commercial or experimental pyrethroids. West German Patent DT-OS No. 27 33 740 describes similar compounds having a substituted or unsubstituted phenyl group in place of the naphthyl group, and A is the group Y where $Y^1$ to $Y^6$ are all hydrogen, R being (a), (c) or (e). Other related phenyl derivatives are described in our copending Australian applications Nos. 19829/76 (A=X) and PD2818/77 (A=Y).

U.S. Pat. No. 4,053,631 describes compounds of the formula I in which A is a lower alkylidene group, i.e. >CH—$R^1$, wherein $R^1$ is $C_1$-$C_4$ alkyl, and R is the group (c). These compounds are described as systemic insecticides.

The acid of the present invention (formula I, R=H) and its esters are novel.

The preferred groups for R are (a), (c) and (e). When A=X, it is preferred that $X^1=X^2=$Cl or F and $X^3=X^4=$H. When A=Y it is preferred that $Y^1=Y^2=Y^3=Y^4=$F and $Y^5=Y^6=$H.

Specifically preferred compounds are as follows:

3'-phenoxybenzyl 1-(2-naphthyl)-2,2,3,3-tetrafluorocyclobutane carboxylate

3'-phenoxybenzyl 2,2-difluoro-1-(2-naphthyl)-cyclopropane carboxylate

α-cyano-3'-phenoxybenzyl 1-(2-naphthyl)-2,2,3,3-tetrafluorocyclobutane carboxylate α-cyano-3'-phenoxybenzyl 2,2-difluoro-1-(2-naphthyl)-cyclopropane carboxylate α-cyano-3'-phenoxybenzyl 2,2-dichloro-1-(2-naphthyl)-cyclopropane carboxylate The compounds of formula I in which R is one of groups (a) to (f) are extremely active as insecticides, having an insecticidal activity an order of magnitude greater than most known insecticides. These compounds also possess the property of contact repellency to insects and are generally more active against flies than the compounds of our aforementioned copending applications.

As well as a high level of insecticidal activity the compounds of the invention (R=(a) to (f)) have a low toxicity to mammals and fish. Their toxicity is so low that the compounds may be used systemically in animals to kill blood sucking insects, ticks and the like. For this use the compounds may be administered orally (either by direct dosing or in food) or by injection. If the compounds are administered in the food, the compound not absorbed by the animal will be excreted in the faeces and give control of flies and other dung breeding species. These properties make these compounds particularly useful for insect control in situations where animals are reared in crowded conditions, e.g. battery rearing of hens or lot-feeding of cattle.

The low toxicity of the compounds towards fish means that these compounds are also particularly useful for insect control in irrigated rice fields in S.E. Asia where the irrigation water is also used for fish culture.

In addition to systemic use these compounds can be utilized in the conventional insecticidal methods and formulations.

The compounds of formula I in which R=H or lower alkyl are useful as intermediates in the preparation of the other esters with R=(a) to (e) as shown below.

The compounds of formula I are optically active and can be resolved into their optical isomers by conventional methods. The invention thus includes the individual optical isomers of the compounds as well as the racemic forms.

It should also be noted that the insecticidal activities of the optical isomers of the compounds I with R=(a) to (f) may differ by an order of magnitude or more.

The invention also includes methods for the synthesis of the compounds I.

The compounds I in which R is one of the groups (a) to (f) may be prepared by esterification of the free acid (formula I, R=H) with the appropriate alcohol R OH, where R is one of the groups (a) to (f). Such esterification may be carried out by any suitable known method, e.g., by direct reaction or by prior conversion of the acid and/or the alcohol to a suitable reactive derivative, or by an ester interchange reaction between the alcohol R—OH (R=(a) to (f)) and a lower alkyl ester of the acid.

The free acid and its lower alkyl esters (formula I, R=H or lower alkyl) are made by reacting the appropriate 2-naphthylacrylate ester of formula II

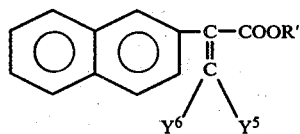

wherein R' is a lower alkyl group and $Y^5$ and $Y^6$ are as defined above with the carbene $:CX^1X^2$ or the olefin $Y^1Y^2C=CY^3Y^4$ (where $X^1$, $X^2$, $Y^1$, $Y^2$, $Y^3$ and $Y^4$ are as defined above) to produce, respectively, the compounds of formula I wherein A is X or Y, as defined above, and R is lower alkyl provided that $Y^5$ and $Y^6$ in formula II are always hydrogen when the carbene reactant is used.

The esters II in which $Y^5=Y^6=H$ may be obtained according to the following general procedure:

(1) A lower alkyl ester of 2-naphthylacetic acid (V) is condensed with a di(lower alkyl) oxalate in the presence of a basic catalyst, to produce a sodium enolate salt (IV).

(2) The solution of the enolate salt is acidified to give the corresponding naphthyl oxaloacetate (III).

(3) The compound III is reacted with formaldehyde under alkaline conditions to give the naphthyl hydroxymethyl acetate which on dehydration (sometimes spontaneously) yields the naphthylacrylic ester (II).

This reaction sequence is illustrated in the following overall reaction scheme. It will be appreciated that the specific acids and bases indicated may be replaced by other suitable compounds. Also lower alkyl esters, other than the ethyl esters shown may be employed.

(Np=2-naphthyl).

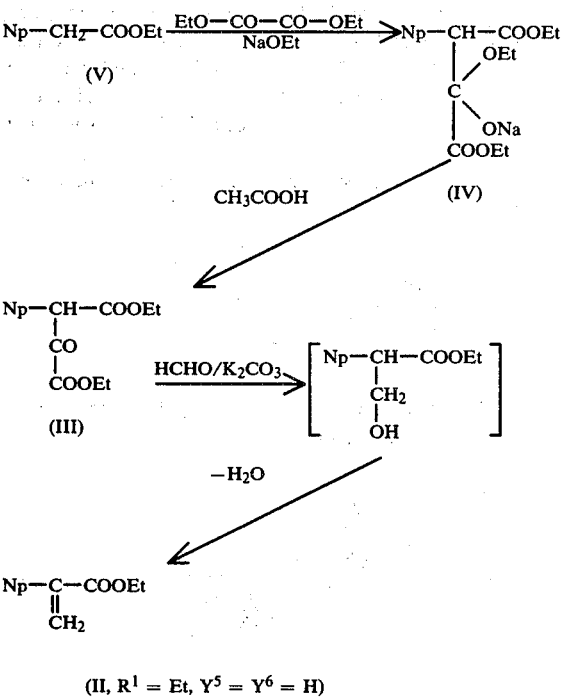

(II, $R^1$ = Et, $Y^5 = Y^6$ = H)

When $Y^5=Y^6=F$, the esters II can be made according to the method similar to that described by D. G. Naae and D. J. Burton, *Synthetic Communications*, 3, 197–200 (1973). In this method the appropriate 2-naphthyl keto ester of formula VI is reacted with dibromodifluoromethane ($CBr_2F_2$) in the presence of 2 moles of tris (dimethylamino)phosphine and a suitable solvent such as diglyme or triglyme

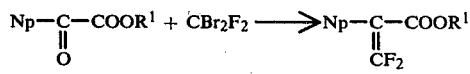

IV           II ($Y^5 = Y^6$ = F)

where Np=2-naphthyl and $R^1$ is a lower alkyl group.

The radical $:CX^1X^2$ may be generated by one of the following reactions:

(a) Where $X^1=Cl$ and $X^2=F$, Cl or Br; by reaction of the appropriate haloform $HCX^1{}_2X^2$ or $HCX^1X^2{}_2$ with alkali in the presence of a phase transfer catalyst, such as triethylbenzylammonium chloride, for example:

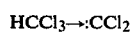

HCCl$_2$F→:CClF

HCBr$_2$Cl→:CBrCl (b) Where X$^1$=X$^2$=F or Cl; from CF$_2$Cl—COONa or CCl$_3$—COONa respectively.

(c) Where X$^1$=X$^2$=CH$_3$; from

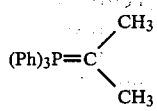

The general approach to formation of the esters of the invention is as follows:

Np—A—COOEt→NpA—COOH

Np—A—COOH→NpA—COCl

Np—A—COCl+ROH→NpA—COOR where Np is the 2-naphthyl group and R is one of the groups (a) to (e) defined above.

Alternatively the ethyl ester can be directly converted as follows:

Np—A—COOEt+ROH→Np-A-COOR

The new compounds described herein may be dissolved in a suitable organic solvent, or mixture of solvents, to form solutions or brought into aqueous suspension by dispersing organic solvent solutions of the compounds in water, to provide useful liquid compositions, which may be incorporated, for example, into aerosol-type dispersions with the usual propellants.

The compounds may also be incorporated in solid compositions which may include inert solid diluents or carriers, to form useful solid compositions. Such compositions may also include other substances such as wetting, dispersing or sticking agents, and may be prepared in granular or other forms to provide slow release of the compounds over an extended period of time. The compounds may be employed in such compositions either as the sole toxic agent or in combination with other insecticides such as pyrethrum, rotenone, or with fungicidal or bactericidal agents, to provide compositions useful for household and agricultural dusts and sprays, textile coating and impregnation, and the like.

For systemic use, liquid compositions may be formulated for injection or oral administration. Solid compositions may also be administered orally.

In particular, the compounds of the invention may be advantageously combined with other substances which have a synergistic or potentiating action. Generally such substances are of the class of microsomal oxidase inhibitors i.e., they inhibit the detoxification of insecticides in insects produced by the action of oxidative enzymes. Typical substances of this type are the pyrethrin synergists of which the following are examples:

| Common Name | Chemical Name |
|---|---|
| Piperonyl butoxide | α[2-(2-butoxyethoxy)ethoxy]-4,5-methylenedioxy-2-propyl-toluene |
| Piperonyl cyclonene | 3-hexyl-5(3,4-methylenedioxy-phenyl)-2-cyclohexanone |
| "Sesoxane" (Sesamex) | 2-(3,4-methylenedioxy-phenoxy)- |
| | 3,6,9-trioxaundecane |
| "Sulfoxide" | 1,2-(methylenedioxy-4-[2-(octylsulfinyl)propyl]-benzene |
| n-Propyl isome | dipropyl-5,6,7,8-tetrahydro-7-methylnaphtho-[2,3-d]-1,3-dioxole-5,6-dicarboxylate |

("Sesoxane", "Sesamex" and "Sulphoxide" are Registered Trade Marks).

We have found that 'Sesoxane' (made by Shulton Inc., Clifton, N.J., U.S.A.) is particularly useful as a potentiator. The amount of 'Sesoxane' used may vary from 1/1000th to five times the weight of the compound I the preferred range bring from about 1/100th to an equal part by weight. Piperonyl butoxide also is a useful potentiator in similar amounts.

The preparation and properties of the compounds of the invention are illustrated by the following specific examples. It should be noted, of course, that these examples are intended to be illustrative of the methods and procedures utilized in preparing the compounds and that they are not intended to be restrictive or to be regarded as embodying the only way in which the compounds can be formed and recovered.

EXAMPLE 1

(a) Ethyl 2-(2-naphthyl) acrylate

Ethyl 2-naphthyl acetate (21.4 g) was added to a slurry of sodium ethoxide (2.53 g) and diethyl oxalate (16.08 g) at ice temperature and reacted for 18 hours, the reaction mixture being allowed to warm up to room temperature over that period. The solid formed was filtered, washed with ether, and added to a 50% acetic acid in ice-water solution. The oil formed was extracted with ether and the ether layer washed with sodium bicarbonate, separated, and dried over anhydrous sodium sulphate. To this oil formaldehyde (10.2 ml; 38.5%), ether (50 ml) and potassium carbonate (9.0 g) were added and the slurry stirred overnight. Another 5 ml of formaldehyde and potassium carbonate (0.5 g) were added and the suspension stirred for an additional 0.5 hours. The oil (18.6 g) was purified by chromatography on a silica gel column using methylene chloride as an eluent. The yield of the pure acrylate was 11.89 g. The unstable product was identified by p.m.r. and i.r. spectra and used further without purification in the next step. The p.m.r. spectrum was: ethyl CH$_3$ (3H) triplet δ=1.2 ppm; ethyl CH$_2$ (2H) quartet δ=4.3 ppm; acrylate protons (2H) doublet δ=6.20 ppm; aromatic protons (7H) multiplet δ=7.65 ppm.

(b) Ethyl-1-(2-naphthyl)-2,2,3,3-tetrafluorocyclobutane carboxylate

The naphthyl acrylate together with 5 ml of tetrafluoroethylene and benzene (20 ml) were charged into a steel autoclave and heated for 24 hours at 180° C. and 6 hours at 200° C. After cooling, the contents of the autoclave was dissolved in ether and dried over anhydrous sodium sulphate. After evaporation of the solvents, the residual oil (6.02 g) was chromatographed on a silica gel column using methylene chloride/petroleum ether (b.p. 40°-60° C.) as eluent. The product fraction was distilled under vacuum. The ester (yield 71.6%) was identified by p.m.r. and i.r. spectra and used for the next step without further purification. The p.m.r. spectrum was:

ethyl CH$_3$ (3H) triplet at δ=1.2 ppm; ethyl CH$_2$ (2H) quartet at δ=4.2 ppm; cyclobutane CH$_2$ (2H) multiplet at 3.45 ppm; aromatic protons (7H) multiplet at δ=7.65 ppm.

(c) 1-(2-naphthyl)-2,2,3,3-tetrafluorocyclobutane carboxylic acid

The ester (4.36 g) was hydrolysed by refluxing in 0.1 N sodium hydroxide in ethanol. The reaction mixture was acidified and the solid acid formed filtered and recrystallised from methylene chloride/petroleum ether (b.p. 60°-80° C.). The pure acid (3.41 g) was obtained as white powder m.p. 131°-2° C.). Analysis: Found C, 59.92; H, 3.44; F, 25.2. C$_{15}$H$_{10}$F$_4$O$_2$ requires C, 60.41; H, 3.38; F, 25.5%. The p.m.r. spectrum was: cyclobutane CH$_2$ (2H) multiplet at δ=3.4 ppm; aromatic protons (7H) multiplet at δ=7.7 ppm; acid proton (1H) singlet at δ=10.45 ppm. The acid proton exchanges with D$_2$O.

EXAMPLE 2

2,2-Difluoro-1-(2-naphthyl)-cyclopropanecarboxylic acid

Ethyl 2-(2-naphthyl)-acrylate (4.28 g) was dissolved in sulfolane 20 ml. Sodium chlorodifluoroacetate (9.1 g) was added in portions to the solution, heated to 160° C., over 35 minutes. The reaction mixture was cooled, quenched into ice water, then extracted with ether. The ether layer was washed several times with water and after separation dried over anhydrous sodium sulphate. After evaporation of the ether, the residual dark oil was chromatographed on silica gel using petroleum ether (b.p. 40°-60°)/methylene chloride mixture as eluent. The major fraction (4.05 g) was distilled under vacuum to yield the product as a yellow oil (3.92 g; 71%). The ester was identified from i.r. and p.m.r. spectra and hydrolysed by refluxing in 1 N sodium hydroxide/ethanol solution. On acidification and extraction the solid acid was recrystallised from petroleum ether/methylene chloride to yield the acid as a white solid, m.p. 190°-2°.

Analysis: Found C, 67.19; H, 4.01; F, 15.6; C$_{14}$H$_{10}$F$_2$O$_2$ requires C, 67.73; H, 4.06; F, 15.3%.

EXAMPLE 3

2,2-Dichloro-1-(2-naphthyl)-cyclopropane carboxylic acid

Ethyl 2-(2-naphthyl)-acrylate (3.86 g) was dissolved in chloroform (4.3 g) tetraethylbenzyl ammonium chloride (36 mg) was added and sodium hydroxide (9 ml; 50%) added dropwise over 10 minutes at room temperature. The reaction mixture was stirred for an additional 2 hours and then quenched in ice water and extracted with ether. The solvent layer was washed sequentially with water, dilute hydrachloric acid and water again, and dried over anhydrous sodium sulphate. After evaporation of the solvents, the oily residue was chromatographed on silica gel using petroleum ether (b.p. 60°-80°) methylene chloride as eluent. The main fraction, a yellow oil (4.85 g), was distilled under vacuum to yield the ethyl ester of 2,2-dichloro 1-(2-naphthyl)cyclopropanecarboxylic acid identified by its i.r. and p.m.r. spectra. This ester was hydrolysed by refluxing in a 1 N sodium hydroxide/ethanol solution. On acidification the cyclopropane acid was obtained as a solid. This was recrystallised from petroleum ether (b.p. 40°-60°)/methylene chloride to yield (0.97 g; 31%) of the acid, m.p. 154°-5° C.

Analysis: Found C, 59.58; H, 3.57; Cl, 24.8; C$_{14}$H$_{10}$Cl$_2$O$_2$ requires C, 59.81; H, 3.59; Cl, 25.2%.

EXAMPLE 4

Formation of m-phenoxybenzyl esters and α-cyano m-phenoxybenzyl esters

Each of the acids produced in Examples 1(c), 2 and 3 (2 m.mol) was refluxed with thionyl chloride (0.48 g) for 1 hour. The thionyl chloride was evaporated and the acid chloride dissolved in petroleum ether (b.p. 40°-60°; 10 ml). This solution was added to a cooled solution of pyridine (0.24 g) and m-phenoxybenzyl alcohol (0.40 g) or α-cyano-m-phenoxybenzyl alcohol (0.68 g), in benzene/petroleum ether (b.p. 40°-60°). The solution was cooled and stirred for 18 hours at room temperature. It was then quenched in ice-water, extracted with ether and after washing with water, sodium bicarbonate solution and water the solvent layer was dried with anhydrous sodium sulphate, evaporated and the oily residues of the products were chromatograhed on silica gel using petroleum ether (b.p. 40°-60°) methylene chloride as eluents. The structures of the esters were confirmed by i.r. and p.m.r. spectroscopy. The p.m.r. spectra of the esters contained peaks from the cyclobutane and aromatic protons as for the corresponding acids. In addition the m-phenoxybenzyl esters had: benzylic protons (2H) singlet at δ=5.15 ppm; and aromatic protons (9H) multiplet at δ=7.4 ppm. The α-cyano-m-phenoxybenzyl esters had: benzylic proton (1H) singlet at δ=6.35 ppm; aromatic protons (9H) multiplet at δ=7.4 ppm.

EXAMPLE 5

Insecticidal Activity

Compounds were tested for activity against a dieldrin susceptible strain (LBB) of the Australian sheep blowfly *Lucilia cuprina*, which had been collected before dieldrin usage in the field.

The test compound was applied in acetone solution, 0.5 μl dispensed with a micropipette to the dorsum of the thorax of 2-3 day old females. Adult flies were fed on water and sugar-only and maintained at 25° C. and 60-70% RH. The mortalities were determined after 24 hours. Moribund flies were regarded as dead. The LD$_{50}$ values, in terms of concentration, were interpolated from a probit/log dose graph using a computer program.

Comparative LD$_{50}$ figures for DDT and dieldrin are 0.17 and 0.025 μg/insect.

Potentiation with "Sesoxane" was investigated by pretreating the insects with 1 μg of the potentiator, applied in an acetone solution. The mortalities were compared with acetone and acetone/potentiator (only) controls.

The compounds tested were as follows:
A. 3'phenoxybenzyl 1-(2-naphthyl)-2,2,3,3-tetrafluorocyclobutane carboxylate
B. 3'-phenoxybenzyl 2,2-difluoro-1-(2-naphthyl)-cyclopropane carboxylate
C. α-cyano-3'-phenoxybenzyl 1-(2-naphthyl)-2,2,3,3-tetrafluorocyclobutane carboxylate
D. α-cyano-3'-phenoxybenzyl 2,2-difluoro-1-(2-naphthyl)cyclopropane carboxylate
E. α-cyano-3'-phenoxybenzyl 2,2-dichloro-1-(2-naphthyl)cyclopropane carboxylate
F. α-cyano-3'-phenoxybenzyl 3,3-difluoro-1-(2-naphthyl)cyclobutane carboxylate.

The results of the tests are set out in Table 1.

TABLE 1

| Compound | A | R | LD₅₀ μg/♀ insect alone | with synergist |
|---|---|---|---|---|
| A. | −C(F)(H)−C(F)(F)−C(H)(H)−C(F)(F)− (tetrafluoro chain) | (a) | 0.25 | 0.028 |
| B. | cyclopropyl with H,H / C,F,F | (a) | 2.9 | 0.095 |
| C. | −C(F)(H)−C(F)(F)−C(H)(H)−C(F)(F)− | (c) | 0.028 | 0.0009 |
| D. | cyclopropyl H,H / F,F | (c) | 0.9 | 0.09 |
| E. | cyclopropyl H,H / Cl,Cl | (c) | 0.8 | 0.02 |
| F. | −C(H)(H)−C(H)(H)−C(H)(F)−C(F)(F)− | (c) | 0.18 | 0.002 |

EXAMPLE 6

This example demonstrates the use of these compounds as systemic insecticides in animals.

Female white mice (weight approximately 20 g.) with shaved backs were injected subcutaneously with 100 μl of olive oil containing a known concentration of the compound under test. Approximately 20 stable flies (*Stomoxys calcitrans*) were placed in a cage. One hour later a restrained mouse in a mesh covered container was placed into the cage. This was repeated for a range of concentrations. The treated mice and untreated controls were exposed to the feeding flies for 18 hours. After that period the percentage of dead flies in each cage was counted and $LD_{100}$ and $LD_{50}$ calculated from a probit/concentration in oil curve.

| Compound (see Example 5) | Results $LD_{100}$ | $LD_{50}$ |
|---|---|---|
| A | 1000 ppm | 800 ppm |
| B | 1000 ppm | 800 ppm |
| C | 1000 ppm | 400 ppm |

EXAMPLE 7

The following are examples of insecticidal compositions in accordance with the invention. All parts are by weight.

(a) Spray formulation

The following composition is adapted for spray application.

| | |
|---|---|
| Compound of formula I | 4.0 |
| "Sesoxane" or Piperonyl butoxide | 1.0 |
| Deodorized kerosene | 79.4 |
| Alkylated naphthalene | 16.0 |

(b) Aerosol

The following materials are metered into a suitable 'bomb' container sealed and equipped with a valve in the usual way.

| | |
|---|---|
| Compound of formula I | 3.0 |
| Potentiator | 1.0 |
| Methylene chloride | 10.0 |
| 'Freon 12' | 43.0 |
| 'Freon 11' | 43.0 |

(c) Water dispersable powder

The following powdered composition is intended for dispersing in water for application as a spray.

| | |
|---|---|
| Compound of formula I | 50.0 |
| Synthetic fine silica | 30.0 |
| Alkyl aryl sodium sulphonate | 1.5 |
| Methyl cellulose (15 cp.) | .25 |
| Attapulgite | 8.25 |

(d) Solution for oral administration

The following solution may be administered orally by gavage or drenching to obtain systemic protection against biting insects.

| | |
|---|---|
| Compound of formula I | 10.0 |
| Olive oil (B.P. grade) | 90.0 |

We claim:

1. The (+), (−), and (±) forms of the compounds of the general formula I

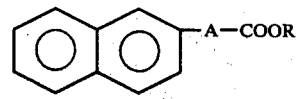

wherein R is one of the following groups (a) to (f):

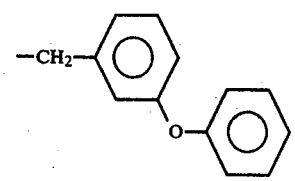

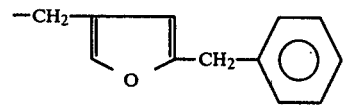

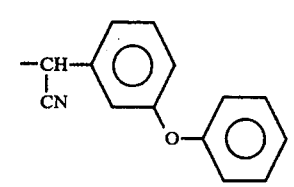

-continued

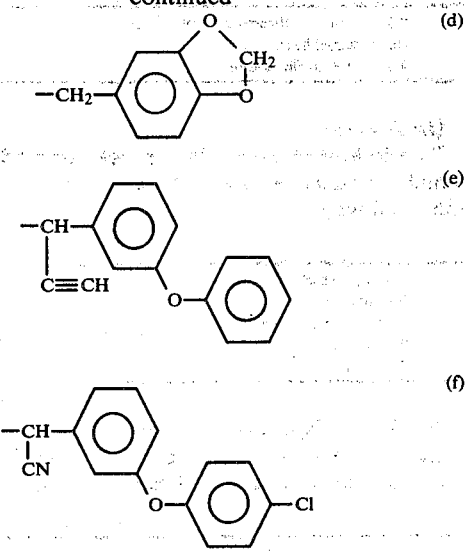

and A is the group Y

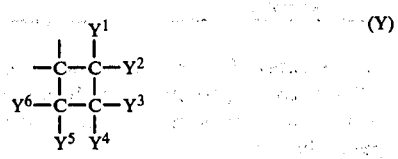

wherein $Y^1$, $Y^2$, $Y^3$, $Y^4$, $Y^5$, and $Y^6$ are the same or different groups and each is hydrogen or a fluoro, bromo, chloro, or methyl group.

2. The compound of claim 1 wherein R is (a).
3. The compound of claim 1 wherein R is (b).
4. The compound of claim 1 wherein R is (c).
5. The compound of claim 1 wherein R is (d).
6. The compound of claim 1 wherein R is (e).
7. The compound of claim 1 wherein R is (f).
8. The compound of claim 1 wherein $Y^1$, $Y^2$, $Y^3$, $Y^4$, $Y^5$, and $Y^6$ are the same or different groups and each is a fluoro, bromo, or chloro group.
9. Compounds as claimed in claim 1, characterised in that R is one of the groups (a), (c) and (e) as defined in claim 1.
10. Compounds as claimed in claim 1, characterised in that at least two of the groups $Y^1$ through $Y^4$ are F and the remainder, if any, are H and $Y^5=Y^6=H$.

11. The (+), (−) and (±) forms of 3'-phenoxybenzyl 1-(2-naphthyl)-2,2,3,3-tetrafluorocyclobutane-carboxylate.

12. (+), (−) and (±) forms of α-cyano-3'-phenoxybenzyl 1-(2-naphthyl)-2,2,3,3-tetrafluorocyclobutanecarboxylate.

13. The (+), (−) and (±) forms of α-cyano-3'-phenyxybenzyl 3,3-difluoro-1-(2-naphthyl)-cyclobutanecarboxylate.

14. Insecticidal compositions, characterised in that they comprise an insecticidally effective amount of one or more of the compounds of formula I, as stated in claim 1, where R is one of the groups (a) to (f), incorporated in a suitable inert liquid or solid carrier.

15. Insecticidal compositions as claimed in claim 14, characterised in that they additionally contain at least one synergistic or potentiating agent of the class of microsomal oxidase inhibitors.

16. Insecticidal compositions as claimed in claim 15, characterised in that the synergist or potentiator is a pyrethrin synergist.

17. Insecticidal compositions as claimed in claim 15, characterised in that the synergist is one of the following:

α[2-(2-butoxyethoxy)ethoxy]-4,5-methylenedioxy-2-propyltoluene;
3-hexyl-5(3,4-methylenedioxyphenyl)-2-cyclohexanone;
2-(3,4-methylenedioxy-phenoxy)-3,6,9-trioxaundecane;
1,2-(methylenedioxy)-4-[2-(octylsulfinyl)propyl]benzene;
dipropyl-5,6,7,8-tetrahydro-7-methylnaphtho-[2,3-d]-1,3-dioxole-5,6-dicarboxylate.

18. Insecticidal compositions as claimed in claim 15, characterised in that the synergist is "Sesoxane" or piperonyl butoxide used in an amount from 1/1000th to 5 times the weight of the compound I.

19. Insecticidal compositions as claimed in claim 15, characterised in that the amount of Sesoxane or piperonyl butoxide used is from about 1/100th to an equal part by weight per part of the compound I.

20. A method of controlling insects comprising applying an insecticidally effective amount of a compound of the formula of claim 1 to an area requiring insect control.

21. A method of controlling insects comprising applying an insecticidally effective amount of the composition of claims 14, 15, 17, 18 or 19 to an area requiring insect control.

* * * * *